United States Patent
Cheng

(10) Patent No.: US 10,046,051 B2
(45) Date of Patent: Aug. 14, 2018

(54) DRUG CARRIER AND METHOD OF USING THE SAME

(71) Applicant: LINKWIN TECHNOLOGY CO., LTD., Taichung (TW)

(72) Inventor: Yi-Ching Cheng, Taichung (TW)

(73) Assignee: LINKWIN TECHNOLOGY CO., LTD., Taichung (TW)

( * ) Notice: Subject to any disclaimer, the term of this patent is extended or adjusted under 35 U.S.C. 154(b) by 146 days.

(21) Appl. No.: 15/211,853

(22) Filed: Jul. 15, 2016

(65) Prior Publication Data

US 2017/0157252 A1 Jun. 8, 2017

(30) Foreign Application Priority Data

Dec. 8, 2015 (TW) .............................. 104141093 A

(51) Int. Cl.
*A61N 1/30* (2006.01)
*A61K 41/00* (2006.01)
(Continued)

(52) U.S. Cl.
CPC .............. *A61K 41/00* (2013.01); *A61B 5/055* (2013.01); *A61B 5/0515* (2013.01); *A61K 9/0009* (2013.01); *A61K 9/0019* (2013.01); *A61K 41/0042* (2013.01); *A61K 47/02* (2013.01); *A61K 47/10* (2013.01); *A61K 47/6923* (2017.08); *A61K 47/6953* (2017.08); *A61K 51/0491* (2013.01); *A61M 37/0092* (2013.01); *A61N 1/30* (2013.01); *A61N 1/306* (2013.01); *A61N 2/002* (2013.01); *A61N 5/022* (2013.01); *A61N 5/062* (2013.01); *A61N 5/10* (2013.01); *A61B 6/037* (2013.01); *A61N 5/0625* (2013.01); *A61N 5/1001* (2013.01);
(Continued)

(58) Field of Classification Search
CPC .. A61K 41/00; A61K 47/6953; A61K 9/0009; A61N 2005/1098; A61B 1/00158
See application file for complete search history.

(56) References Cited

U.S. PATENT DOCUMENTS 4,564,363 A * 1/1986 Bagnall ..................... A61D 7/00
                                                    222/641
6,240,312 B1 * 5/2001 Alfano ............... A61B 1/00016
                                                    128/903
(Continued)

FOREIGN PATENT DOCUMENTS

TW         I445661 B      7/2014

*Primary Examiner* — Rebecca E Eisenberg
(74) *Attorney, Agent, or Firm* — Lynette Wylie; Apex Juris, pllc.

(57) ABSTRACT

A drug carrier and a method of using the same are provided, wherein the drug carrier includes a base made of a carbon fiber which is magnetic and has a first polarity, a positioning member connected to the base, and is adapted to be positioned and move to a target location by guiding of at least an energy field, and a connector connected to the positioning member and a drug with two ends respectively, wherein the connector has a second polarity opposite to the first polarity, and is recognized by an organism and digested in the organism. The method includes the steps of: injecting the drug carrier into an organism; positioning the drug carrier to a target location within the organism by an equipment; and releasing the drug from the drug carrier by an external energy.

19 Claims, 2 Drawing Sheets

(51) Int. Cl.
  *A61B 5/055* (2006.01)
  *A61K 9/00* (2006.01)
  *A61K 47/02* (2006.01)
  *A61K 47/10* (2017.01)
  *A61K 51/04* (2006.01)
  *A61M 37/00* (2006.01)
  *A61N 2/00* (2006.01)
  *A61N 5/02* (2006.01)
  *A61N 5/06* (2006.01)
  *A61N 5/10* (2006.01)
  *A61B 5/05* (2006.01)
  *A61K 47/69* (2017.01)
  *A61B 6/03* (2006.01)
  *A61N 5/067* (2006.01)

(52) U.S. Cl.
  CPC ............... *A61N 2005/067* (2013.01); *A61N 2005/0659* (2013.01); *A61N 2005/1087* (2013.01); *A61N 2005/1098* (2013.01)

(56) References Cited

U.S. PATENT DOCUMENTS

| | | | |
|---|---|---|---|
| 9,814,786 B2* | 11/2017 | Bovin | A61K 31/7028 |
| 2003/0135153 A1* | 7/2003 | Hagemeier | A61B 17/3468 604/59 |
| 2005/0043617 A1* | 2/2005 | Frisch | A61B 1/041 600/431 |
| 2006/0015088 A1* | 1/2006 | Andrae | A61K 9/0009 604/890.1 |
| 2006/0100476 A1* | 5/2006 | Biscotti | A61M 37/0069 600/7 |
| 2008/0033569 A1* | 2/2008 | Ferren | A61B 34/20 623/23.7 |
| 2008/0214894 A1* | 9/2008 | Wedel | A61B 1/00158 600/118 |
| 2009/0005833 A1* | 1/2009 | Cameron | A61N 1/36082 607/45 |
| 2010/0022412 A1* | 1/2010 | Rigatti | C12Q 1/6837 506/17 |
| 2011/0017222 A1* | 1/2011 | Li | A61N 2/06 128/899 |
| 2012/0035437 A1* | 2/2012 | Ferren | A61B 1/041 600/302 |
| 2013/0204181 A1* | 8/2013 | Liu | A61B 8/0833 604/28 |
| 2013/0303847 A1* | 11/2013 | Sitti | A61B 1/00158 600/104 |
| 2014/0187862 A1* | 7/2014 | Nishihara | A61B 1/00156 600/118 |
| 2014/0330257 A1* | 11/2014 | Hyde | A61M 5/14276 604/891.1 |
| 2015/0240411 A1* | 8/2015 | Slamborova | C04B 35/62844 435/188 |
| 2015/0351856 A1* | 12/2015 | Choi | A61B 5/6861 604/514 |
| 2016/0022123 A1* | 1/2016 | Katznelson | A61B 1/00158 600/118 |
| 2016/0038611 A1* | 2/2016 | Vile | A61K 8/498 424/499 |
| 2017/0100539 A1* | 4/2017 | Hood | A61M 5/172 |

* cited by examiner

DRUG CARRIER AND METHOD OF USING THE SAME

BACKGROUND OF THE INVENTION

1. Technical Field

The present invention relates generally to a drug delivery system without any active principle, and more particularly to a drug carrier and a method of using the same.

2. Description of Related Art

In addition to the desired therapeutic effect of a drug or medication, a side effect usually occurs and is regarded as an undesirable secondary effect. Take chemotherapeutic agents for example, the powerful drug toxicity not only kills rapidly growing cancer cells but also harm perfectly healthy cells, which seriously damages the immune system of patients. Accordingly, target therapy and drug delivery systems are developing in recent years to deliver drugs to the lesion for reducing side effects.

However, some specific structures in human body hinder drugs from reaching the lesions. For example, the blood-brain barrier (BBB) limits drugs to enter the lesion in the brain. Actually, less than 20% of drugs can penetrate through the BBB into the brain, and even some molecules are severely restricted to pass across the BBB. Therefore, there are still many difficulties in the treatment of brain diseases.

In light of this, the applicant is devoted to seek useful materials and methods as a possible drug delivery system to improve the drug targeting efficiency, and reduce the adverse drug reactions.

BRIEF SUMMARY OF THE INVENTION

In view of the above, the primary objective of the present invention is to provide a drug carrier and a method of use the same, which carries and exactly delivers drugs to the lesions in the human body.

The present invention provides a drug carrier for carrying and delivering a drug to a target location, including a base, a positioning member, and a connector. The base is made of a carbon fiber, which is magnetic and has a first polarity. The positioning member is connected to the base, wherein the positioning member is adapted to be positioned and move to the target location by guiding of at least an energy field. The connector is connected to the positioning member with an end thereof and the drug with another end thereof, wherein the connector has a second polarity which is opposite to the first polarity; the connector is adapted to be recognized by an organism and digested in the organism.

The present invention further provides a method of using a drug carrier which is connected to a drug, including the steps of: injecting the drug carrier into an organism, wherein the drug carrier includes a nanographite; positioning the drug carrier to a target location within the organism by an equipment, wherein the equipment provides at least an energy field; and releasing the drug from the drug carrier by an external energy. Whereby, the drug act on the target location.

Whereby, with the nanographite and the connector, the drug carrier can release the drug to precise target locations, wherein drugs were not easy to reach the locations by conventional drug delivery systems.

BRIEF DESCRIPTION OF THE SEVERAL VIEWS OF THE DRAWINGS

The present invention will be best understood by referring to the following detailed description of some illustrative embodiments in conjunction with the accompanying drawings, in which.

DETAILED DESCRIPTION OF THE INVENTION

Figure 1:
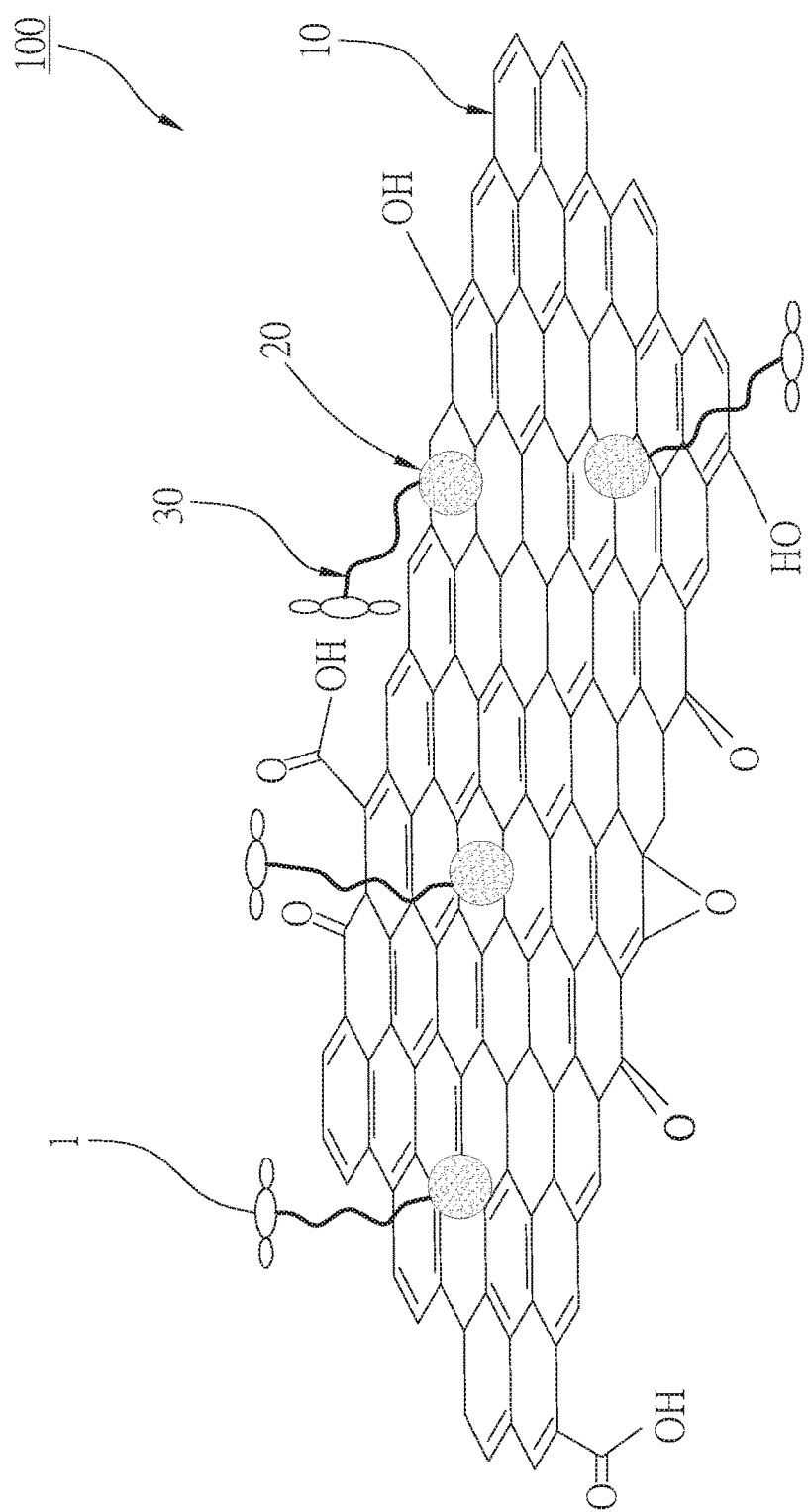
FIG. 1 is a perspective view of a first embodiment of the present invention, showing the drug carrier.

As shown in FIG. 1, the drug carrier 100 is adapted to carry and deliver a drug 1 to a target location in an organism, and includes a base, a positioning member, and a connector. The base, the positioning member, and the connector in the first embodiment are nanographite oxide 10, magnetic bead 20, and polyethylene glycol (PEG) 30.

The nanographite oxide 10 is made of a carbon fiber which is a carbon fiber fabric, wherein the applicant has disclosed the manufacturing method and the carbonizing device of said carbon fiber fabric in an issued U.S. Pat. No. 1,445,661. The nanographite oxide 10 is manufactured by the steps below. First, carbonize the carbon fiber under 1600° C. to 2500° C. or 3000° C. to generate a nanographite with the features of the diamond like carbon, wherein the nanographite has a polarity, and is structurally stable to prevent being connecting to other molecules. Accordingly, the nanographite would not be digested in the organism. Next, chemically bind a plurality of oxide groups to the surface of the nanographite to generate the nanographite oxide 10. After being oxidized, the polarity and the electric conductivity of the nanographite oxide 10 is lowered, which makes the nanographite oxide 10 stable. Moreover, the nanographite oxide 10 is magnetic, and has a first polarity. In another embodiment, the base is nanographite without being oxidized, or has multi-layered structure.

The positioning member is adapted to be positioned and move to the target location by guiding of at least an energy field. In the embodiment, the magnetic bead 20 magnetically attracts the nanographite oxide 10. When an equipment such as a nuclear magnetic resonance equipment provides an energy field (e.g. A magnetic field), the magnetic bead 20 can be positioned and move to the target location by guiding of the magnetic field, which positions the drug carrier 100 to the target location. Furthermore, the positioning member causes a part of the volume in the drug carrier 100 to promote the digestion of the drug carrier 100 by the organism. In more details, if the volume of the drug carrier 100 is too small, the drug carrier 100 could easily accumulate in lungs of the organism because the alveoli are unable to filter the drug carriers 100.

The connector is connected to the positioning member with an end thereof and the drug with another end thereof, wherein the connector has a second polarity which is opposite to the first polarity. In the embodiment, the end of the polyethylene glycol 30 is connected to the magnetic bead 20, and the another end is connected to the drug 1. The polarity and the electrical conductivity of the polyethylene glycol 30 are opposite to that of the nanographite oxide 10 to reduce the polarity and the electrical conductivity of the nanographite oxide 10, and further to increase the stability of the drug carrier 100.

The connector is adapted to release the drug 1 from the drug carrier 100 to the target location after being broken by an external energy, wherein the external energy includes infrared, microwave, laser, ultrasound, or other invisible lights with similar wavelength and energy level to infrared, such as far-infrared. The type of the external energy is selected according to the depth of the target location within the organism. In the first embodiment, the external energy is infrared. Moreover, the connector is also a biomarker, which could be recognized by the organism, and digested with the organism.

Figure 2:
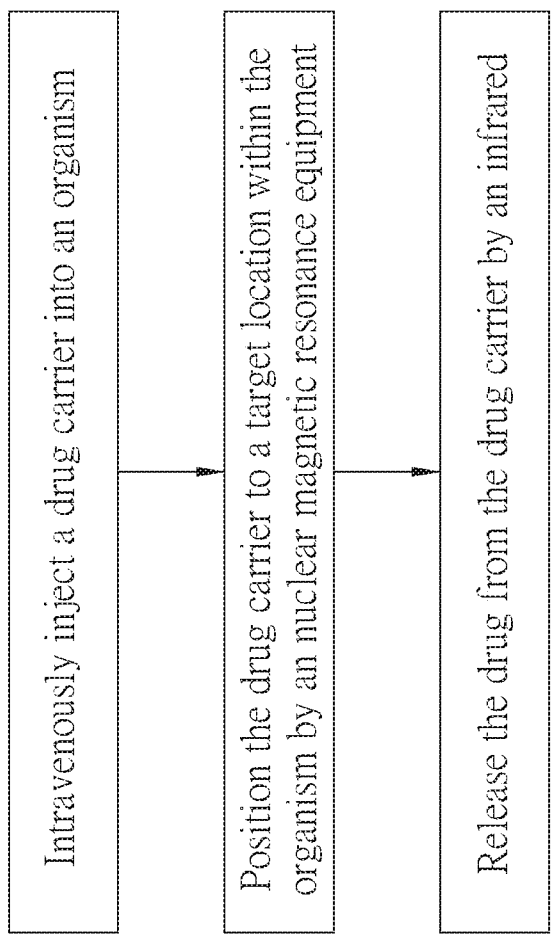
FIG. 2 is a flow chart of the method of using the drug carrier in FIG. 1.

The method of using the drug carrier 100 in treating patients includes the steps shown in FIG. 2. First, intravenously inject the drug carrier 100 and the drug 1 connected to the drug carrier 100 into a patient. Next, position the drug carrier 100 and the drug 1 to the target location within the organism by the magnetic field provide by the nuclear magnetic resonance equipment, wherein the target location is the lesion. Finally, break the connector by an infrared, and release the drug 1 from the drug carrier 100. In addition, said infrared can not only break the connector but also be helpful to kill the abnormal cells at the lesion with the heat energy thereof.

In a second embodiment, the positioning member is a positron-emitting agent instead of the magnetic bead 20, wherein the commonly used positron-emitting agent includes 2-fluoro-2-deoxy-D-glucose (FDG). Additionally, based on the type of the positioning member, the equipment for positioning the drug carrier is a positron emission tomography scanner, which detects tumor lesions according to the characteristic of tumor cells. In more details, the metabolism of glucose in tumor cells is increased.

In addition, the positioning member in a third embodiment is a proton in a high energy state. Similarly, based on the type of the positioning member, the equipment for positioning the drug carrier is a proton radiation therapy equipment, which provides a magnetic field and an electric field. The drug delivery system in the embodiment destroys tumor cells by emitting radiation to the tumor cells. In more details, the magnetic field positions the proton to the target location, while the electric field accelerates the proton.

However, the types of the positioning member and the corresponding equipment are not limited to what described in the abovementioned embodiments.

Furthermore, nanographite is the thinnest but hardest nanomaterial. Therefore, the volume of the drug carrier can be effectively decreased. The overall maximum diameter of the drug carrier in the described embodiments is smaller than 200 nm such that the drug carrier could penetrate some specific structures to reach lesions such as pancreas and brain. Whereby, the drug carrier can act as a novel drug delivery system to solve the conventional problem, and can be specifically applied in diseases in pancreas and brain which were difficult to treat.

It must be pointed out that the embodiments described above are only some preferred embodiments of the present invention. All equivalent structures and methods which employ the concepts disclosed in this specification and the appended claims should fall within the scope of the present invention.

What is claimed is:

1. A drug carrier for carrying and delivering a drug to a target location, comprising:
   a base made of a carbon fiber, which is magnetic and has a first polarity;
   a positioning member connected to the base, wherein the positioning member is adapted to be positioned and move to the target location by guiding of at least an energy field; and
   a connector connected to the positioning member with an end thereof and the drug with another end thereof, wherein the connector has a second polarity which is opposite to the first polarity; the connector is adapted to be recognized by an organism and digested in the organism.

2. The drug carrier of claim 1, wherein the base comprises a nanographite, which is manufactured by carbonizing the carbon fiber.

3. The drug carrier of claim 2, wherein the positioning member comprises a magnetic bead; the at least an energy field comprises a magnetic field.

4. The drug carrier of claim 2, wherein the positioning member comprises a positron-emitting agent.

5. The drug carrier of claim 4, wherein the positron-emitting agent comprises a 2-fluoro-2-deoxy-D-glucose.

6. The drug carrier of claim 2, wherein the positioning member comprises a proton in a high energy state; the at least an energy field comprises a magnetic field and an electric field.

7. The drug carrier of claim 1, wherein the base comprises a nanographite oxide, which is manufactured by the steps of: carbonizing the carbon fiber to a nanographite, and chemically binding a plurality of oxide groups to the nanographite.

8. The drug carrier of claim 7, wherein the positioning member comprises a magnetic bead; the at least an energy field comprises a magnetic field.

9. The drug carrier of claim 7, wherein the positioning member comprises a positron-emitting agent.

10. The drug carrier of claim 9, wherein the positron-emitting agent comprises a 2-fluoro-2-deoxy-D-glucose.

11. The drug carrier of claim 7, wherein the positioning member comprises a proton in a high energy state; the at least an energy field comprises a magnetic field and an electric field.

12. The drug carrier of claim 1, wherein the connector is adapted to release the drug to the target location after being broken by an external energy.

13. The drug carrier of claim 12, wherein the connector comprises a polyethylene glycol.

14. A method of using the drug carrier of claim 1 to carry and deliver a drug to a target location, comprising the steps of:
   connecting the drug to the drug carrier;
   injecting the drug carrier into an organism, wherein the drug carrier comprises a nanographite;
   positioning the drug carrier to the target location within the organism by an equipment, wherein the equipment provides at least an energy field; and
   releasing the drug from the drug carrier by an external energy;
   whereby, the drug acts on the target location.

15. The method of claim 14, wherein the external energy comprises infrared, microwave, laser, or ultrasound.

16. The method of claim 15, wherein the drug carrier comprises a connector connected to the nanographite with an end thereof and the drug with another end thereof; the connector is adapted to release the drug to the target location after being broken by the external energy, and is adapted to be recognized by the organism and digested in the organism.

17. The method of claim 14, wherein the drug carrier comprises a magnetic member connected to the nanographite; the equipment comprises a nuclear magnetic resonance equipment, and the at least an energy field comprises a magnetic field.

18. The method of claim 14, wherein the drug carrier comprises a positron-emitting agent connected to the nanographite; the equipment comprises a positron emission tomography scanner.

19. The method of claim 14, wherein the drug carrier comprises a proton in a high energy state connected to the nanographite; the equipment comprises a proton radiation therapy equipment, wherein the at least an energy field comprises a magnetic field and an electric field.

* * * * *